United States Patent [19]

Ashihara et al.

[11] Patent Number: 4,757,001
[45] Date of Patent: * Jul. 12, 1988

[54] METHOD OF MEASURING BIOLOGICAL LIGAND BY UTILIZING AMYLASE

[75] Inventors: Yoshihiro Ashihara; Yasushi Kasahara, both of Tokyo, Japan

[73] Assignee: Fujirebio Kabushiki Kaisha, Tokyo, Japan

[ * ] Notice: The portion of the term of this patent subsequent to Sep. 8, 2004 has been disclaimed.

[21] Appl. No.: 699,675

[22] Filed: Feb. 8, 1985

[30] Foreign Application Priority Data

Feb. 16, 1984 [JP] Japan ............................. 59-27709
Feb. 16, 1984 [JP] Japan ............................. 59-27710

[51] Int. Cl.$^4$ ............................................ G01N 33/542
[52] U.S. Cl. .......................................... 435/7; 435/22; 435/184; 435/188; 435/201
[58] Field of Search ................ 435/7, 184, 188, 201, 435/22

[56] References Cited

U.S. PATENT DOCUMENTS

| | | | |
|---|---|---|---|
| 4,010,258 | 3/1977 | Murao | 435/184 |
| 4,040,907 | 8/1977 | Ullman | 435/22 |
| 4,279,994 | 7/1981 | Huang | 435/184 |
| 4,322,496 | 3/1982 | Esders | 435/184 |
| 4,337,309 | 6/1982 | McGeeney | 435/22 |
| 4,376,110 | 3/1983 | David | 436/513 |
| 4,474,878 | 10/1984 | Halbert | 435/22 |

FOREIGN PATENT DOCUMENTS

| | | | |
|---|---|---|---|
| 0152091 | 8/1985 | European Pat. Off. | 435/22 |
| 3342736 | 6/1985 | Fed. Rep. of Germany | 435/7 |
| 0078592 | 5/1983 | Japan | 435/184 |
| 183098 | 10/1983 | Japan . | |

OTHER PUBLICATIONS

Robert H. Yolken Reviews of Infections Diseases 4(1) pp. 35–45, 48–50, (1982).

*Primary Examiner*—Robert J. Warden
*Assistant Examiner*—Robert Benson
*Attorney, Agent, or Firm*—Burgess, Ryan & Wayne

[57] ABSTRACT

The present invention relates to the method of measuring a biological ligand (1) in a sample containing an amylase (1) derived from a higher animal. This method is characterized by employing a combination of an amylase (2) not contained in the sample and an antibody against the ligand (1) or a ligand (2) capable of reacting with the antibody and an amylase inhibitor of which inhibitory activity against the amylase (1) is stronger than that against the amylase (2). The method of the invention utilizes the emphasis of steric hindrance of the amylase (2) reaction which is carried out at the boundary between solid phase and liquid phase and the specific removal of the influence of the amylase (1) by using the above amylase inhibitor. This method is suitable as a clinical test for the determination of physiological substances and trace components in a humoral fluid such as serum.

10 Claims, 6 Drawing Sheets

METHOD OF MEASURING BIOLOGICAL LIGAND BY UTILIZING AMYLASE

FIELD OF THE INVENTION

This invention relates to a method of measuring a biological ligand, for example, medicinal substances and trace components derived from various diseases in a humoral fluid such as blood.

DISCUSSION OF THE PRIOR ART

The measurement of the concentration in the blood or a drug administered to a patient, such as digoxin and theophylline, is important in the course of appropriate treatment. Moreover, the detection in the blood of the trace components derived from various diseases such as cancer is important in early diagnoses of such diseases.

A humoral fluid such as blood contains various components, and some of them are similar to each other in their molecular weights or physiological properties. Therefore, the measurement of the component requires high specificity and high sensitivity. Furthermore, in order to be utilized as a routine method for diagnosis of a disease, the measuring procedure must of necessity be simple.

Various method for detecting these trace components in blood have been developed, and among them, enzyme immunoassay is widely employed because of its superior sensitivity, specificity and ability to rapidly process a large number of samples. However, in the case of the conventional enzyme immunoassay, the sensitivity is not sufficient and it is not easy to obtain an accurate measurement because of the complicated washing procedures and the transferring of tubes.

The inventors have investigated various enzyme immunoassays using various combinations of a ligand or an antibody and an enzyme or a material having an enzyme inhibitory activity as follows:

The method of measuring a biological ligand which comprises, contacting a ligand (1) to be measured and a conjugate of a ligand (2) having an antigenic determinant common to one or the antigenic determinant(s) of the above ligand (1) and biotin or its derivatives capable of reacting with avidin or streptoavidin with an antibody capable of reacting with the above common antigenic determinant in an aqueous solution, contacting the above combination with avidin, streptoavidin or one of their derivatives capable of reacting with biotin, and measuring the biotin-containing enzyme activity (Japanese Patent Application Kokai No. 142466/1984).

The method of measuring a biological ligand which comprises, contacting a ligand to be measured and an enzyme or a conjugate of an enzyme and a macromolecular substance, with a conjugate of an antibody against the above ligand and an antibody against the above enzyme, or with a conjugate of an antibody against the above ligand, an antibody against the above enzyme and a macromolecular substance in an aqueous solution, and measuring the activity of the enzyme (applicant's U.S. Pat. No. 4,621,848).

The method of measuring a biological ligand which comprises, allowing to coexist a biologically active composition comprising an immobilization phase of an antibody capable of reacting with the ligand (1) to be measured or a biological ligand (2) capable to reacting with the above antibody and an immobilization phase of a biotin-containing enzyme or a biotin-containing enzyme inhibitor, a water-soluble conjugate of the above ligand (2) or the above antibody and a biotin-containing enzyme inhibitor capable of reacting with the above biotin-containing enzyme or a biotin-containing enzyme capable of reacting with the above biotin-containing enzyme inhibitor, and the ligand (1) to be measured in an aqueous solution. and measuring the biotin-containing enzyme activity or the biotin-containing enzyme inhibitory activity of the biological active composition or the aqueous solution (applicants' U.S. Pat. No. 4,649,105).

The method of measuring a biological ligand which comprises, contacting a ligand (1) to be measured and a conjugate of a ligand (2) having an antigenic determinant being common to one of the antigenic determinant(s) of the ligand (1) and a biotin-containing enzyme inhibitor with an antibody capable of reacting with the common antigenic determinant in an aqueous solution, contacting the above conjugate with a biotin-containing enzyme, and measuring the biotin-containing enzyme activity (applicants' U.S. patent application Ser. No. 622,860 now abandoned)

The method of measuring a biological ligand which comprises, using an antibody against the ligand (1) to be measured and an enzyme capable of acting on a water-insoluble macromolecular substance and which conjugate with the above antibody or with a ligand (2) having an antigenic determinant common to one of the antigenic determinant(s) of the ligand (1), contacting the above antibody with the above ligand(s), and contacting the above enzyme with the above macromolecular substance (applicants' U.S. Pat. No. 4,692,404).

They have further investigated the last method, and have found that when an amylase is employed as the enzyme, the ligand (1) can be detected in the highest sensitivity. However, in the case of the sample derived from a higher animal, since it usually contains an amylase, a blank value becomes high which introduces large errors. Accordingly, they have examined various methods in order to lower this blank value. However, when the amylase in a sample was previously inactivated such as by heating or by treating with an acid or an alkali, some ligands in the sample were also denatured or decomposed during the inactivation. On the other hand, when the sample was diluted in order to lower the blank value, the sensitivity to detect the ligand (1) was also lowered. In addition, since these treatments complicate the operation, the introduction of these treatments negate the intention of the inventors to develop a simple method of measuring the ligand (1).

SUMMARY OF THE INVENTION

Thereupon, the inventors have further investigated in order to develop a method of lowering this blank value without lowering its simplicity and high sensitivity, and the object has been achieved by using an amylase inhibitor which specifically inhibits the amylase derived from a higher animal.

The invention will be more clearly understood by reference to the drawings as further described in the Examples wherein.

DETAILED DESCRIPTION OF THE INVENTION

The method of the invention comprises, using an antibody against a biological ligand (1) to be measured, an amylase (2) not contained in the sample and conjugated with the above antibody or a biological ligand (2) against the above antibody, an amylase inhibitor of which the inhibitory activity against the amylase (1) contained in the sample is stronger than that against the amylase (2) and a water-insoluble macromolecular substance capable of being digested by the amylase (2), contacting the above antibody with the ligand (1), in the case that the amylase (2) is bound to the ligand (2), contacting the ligand (2) with the above antibody contacting the above amylase inhibitor with the amylase (1), and thereafter digesting the above macromolecular substance with the amylase (2).

The sample measured by the method of the invention contains an amylase (1) derived from a higher animal. The amylase (1) includes pancreatic amylase and salivary amylase, and the sample containing such an amylase is also usually derived from a higher animal. The kind of the sample is not limited, and includes serum, plasma and urine. In the case of serum and urine, pretreatment is not necessary.

The subject to be measured by the method of the invention is a ligand (1). The ligand (1) is a substance having one or more antigenic determinants, and includes for example, hormones derived from varous endocrince glands, plasma proteins such as immunoglobulin, albumin and ferritin, viral antigens such as HB antigen, bacteria, α-fetoprotein, and carcinoembyonic antigens.

The ligand (2) also has one or more antigenic determinants and at least one antigenic determinant is common to one of the antigenic determinants(s) of the ligand (1). All antigenic determinants of the ligand (2) may be equal to those of the ligand (1), and accordingly, ligand (2) may be identical with the ligand (1).

The antibody used is the antibody against the ligand (1). In the case where the ligand (2) is employed, this antibody should also be the antibody against the ligand (2). That is, in this case, the antibody should be the antibody against this common antigenic determinant. The antibody includes fragments of immunogloblin such as F(ab')$_2$, Fab' and Fab, and a modified one such as introduction of DNP group, acetyl group, biotinyl group or nitro group.

Such an antibody may be produced according to conventional method of producing an antibody. For example, the ligand (1), the ligand (2) or a conjugate of either of these ligands and a protein material is injected once or several times into the subcutaneous region of the back, foot pad or femoral muscle of a warm-blooded animal such as a rabbit, goat, horse, guinea pig and chicken, in an amount of about 0.3 to 2 mg per kg together with an adjuvant, thereby producing the antibody in the humoral fluid such as serum. This humoral fluid, as it is, may be used as the antibody, however, the antibody may preferably be separated according to a conventional isolation method of an immunoglobulin.

On the other hand, the antibody may be produced as a monoclonal antibody. In this case, one of the above antigens is injected several times into the abdominal cavity of a mouse together with an adjuvant, and its spleen is excised. The spleen cell is fused with a mouse myeloma cell by a conventional method involving the use of polyethylene glycol. The hybridoma thus obtained is cultured and cloned, and the cell capable of producing the desired antibody is obtained. This cell is injected into the abdominal cavity of a mouse, and multiplied. Then, ascites are collected, and the desired antibody is separated from the ascites.

In the case where the antibody does not conjugate with the amylase (2) described later, if the amylase (2) activity does not appreciably vary through the reaction of the antibody with the ligand (2) portion of the conjugate which is also described later, a macromolecular compound may preferably be conjugated with the antibody prior to use. Preferred macromolecular compounds are water-soluble, and their molecular weights are greater than about 100,000 daltons. Examples of the macromolecular compounds include polysaccharides and their derivatives such as soluble dextran, carboxymethyl dextran, and dextran having amino group proteins such as gelatin, hemocyanin and ferritin, and polyethylene glycol. The macromolecular compound may be conjugated with the antibody according to the binding method described later.

The amylase (2) does not exist in the sample, and it is conjugated with the above antibody or the ligand (2). This amylase (2) includes α-amylase, β-amylase and glucoamylase. Suitable amylase (2) is different according to the kind of the sample, the kind of the amylase inhibitor described later, etc., and for example, it may be selected from diastase and β-amylase derived from malt, takadiastase derived from a mold fungus, and amylase derived from a bacterium of genus Bacillus.

The amylase (2) is allowed to conjugate with the antibody or the ligand (2). When it is allowed to conjugate with the antibody, the ligand (2) is not used. On the other hand, when it is allowed to conjugate with the ligand (2), the antibody is used as its natural form or conjugated with a macromolecular compound.

The conjugating method of the amylase (2) and the antibody or the ligand (2) may be selected by considering the functional groups of both substances. Such functional groups include, amino groups, carboxyl groups, hydroxyl groups, thiol groups, imidazole groups, phenyl groups, etc. The introduction of amino groups, may be carried out by many methods such as the diisocyanate method, the glutaraldehyde method, the difluorobenzene method, and the benzoquinone method, etc. As the method to introduce an amino group and a carboxyl group, the peptide-binding method of carboxyl group to succinimide ester, the carbodiimide method, the Woodward reagent method are known. The periodate oxidation method (Nakane method) where a bridge between amino group and sugar chain forms is also utilized. In the case of using a thiol group, for example, a carboxyl group is first converted to a succinimide ester, and this ester group is then allowed to react with cysteine to introduce the thiol group, and both thiol groups are introduced by using a thiol-reactive bifunctional cross-linking reagent such as phenylene-bismaleimide. As the method of utilizing a phenyl group, the diazotization method and the alkylation method are utilized. Other than the above, a suitable method may be selected from the various methods described in "Method in Immunology and Immunochemistry" (C. A. Williams et al., 1976, Academic Press N.Y.) and "Koso Meneki Sokutei-ho" (E. Ishikawa et al., 1978, Igaku-shoin (Japan)). The molar ratio of the conjugate is not limited to 1:1, and suitable ratios can be selected. After the conjugating reaction, the conjugate produced is purified by gel filtration, ion-exchange chromatography and affinity chromatography, and lyophilized, if necessary.

When the amylase (2) conjugates with the antibody, the antibody is allowed to contact the ligand (1) to be measured. While, when the amylase (2) conjugate with the ligand (2), the antibody is allowed to contact the ligand (1) and the ligand (2) portion of the conjugate. In the latter case, the order of the contacting is not limited, and either of the ligand (1) and the conjugate may first be allowed to contact the antibody. Of course, both materials may be allowed to contact at the same time. The temperature of the solution is usually kept at about 20° to 45° C., and the pH is usually kept at about 4 to 9. In order to keep the pH constant, a buffer solution such as a phosphate buffer solution and an acetate buffer solution may be employed. Since the suitable amounts of the conjugate and the antibody are different according to their kinds, the kind of the ligand (1), the contacting conditions etc., the amounts may preferably be determined by a preliminary test.

In the case that the antibody does not conjugate with the amylase (2), if the activity of the amylase (2) does not appreciably vary through the reaction of the antibody with the ligand (2) portion of the conjugate, a second antibody may further be allowed to react with the antibody conjugated with the ligand (2) portion. The second antibody may be prepared according to the same method as previously described.

On the other hand, in the case where the antibody conjugate with the amylase (2), the sensitivity is raised one or two orders by adding another antibody against a different antigenic determinant of the ligand (1). This antibody may also be produced according to the conventional method previously described. Since the antibody in the humoral fluid is a mixture of the antibodies recognizing various antigenic determinants, it is necessary that they be separated. The separation may be carried out by affinity chromatography. For example, the ligand (1) is digested by an enzyme or a chemical reagent, and the fragments produced are separated by gel filtration or ion-exchange chromatography. Each fragment was immobilized on a carrier, and thereby the column for affinity chromatography is prepared. The above antibodies mixture is separated by using this column. It is sufficient that the antibodies mixture is separated into two groups. As the production of such a specific antibody, the method of producing a monoclonal antibody by using the cell fusion technique described previously is suitable. A water-soluble macromolecular compound may be bound to the antibody in order to raise the sensitivity. The molecular weight of greater than 1,000 is preferable. Examples of the macromolecular compound include proteins such as albumin and hemocyanin, polysaccharides, polyethylene glycol and polynucleotides. The conjugating method may be selected from the conjugating methods of the amylase (2) previously described. A second antibody may be conjugated with this antibody in order to raise the sensitivity. The second antibody may also be prepared according to the same method as previously described. This second antibody may be added to the antibody prior to contacting with ligand (1) or at the same time.

On the other hand, the amylase (1) derived from a higher animal and contained in the sample is allowed to contact an amylase inhibitor of which the inhibitory activity against the amylse (1) is stronger than that against the amylase (2).

The most desirable amylase inhibitor inactivates all amylases (1) contained in the sample and does not inhibit the amylase (2) of the conjugate. However, it is practically sufficient that the amylase inhibitor inactivates main amylase (1) in the sample. The inactivation is enough to be kept through the measurement, and the activity of the amylase (1) may be recovered after the measurement.

Examples of such an amylase inhibitor include the amylase inhibitor derived from wheat which inhibits both salivary amylase and pancreatic amylase (M. D. O'Donnell et al., Biochim, Biophys. Acta, vol. 422, pp 159–169 (1976)), amylase inhibitor derived from wheat which preferentially inhibits salivary amylase (Japanese Patent Application Kokai No. 85899/1983) and amylase inhibitor AI-B produced by an actinomycetes of genus Streptomyces which preferentially inhibits pancreatic amylase (Japanese Patent Application Kokai No. 2684/1982). Besides, when the amylase (1) contained in the sample is injected into a foreign animal to produce the antibody, this antibody may also be utilized as the amylase inhibitor. These amylase inhibitors may be used jointly.

The temperature and the pH of the solution while the amylase inhibitor is allowed to contact the amylase (1) are usually kept at the same conditions as the contacting the the ligand (1) with the antibody. The suitable amount of the amylase inhibitor is different according to its kind, the kind and the amount of the amylase (1), the kind of the amylase (2), the contacting conditions etc., the amount may preferably be determined by a preliminary test. The amylase inhibitor is usually added prior to the addition of the water-insoluble macromolecular substance. However, since the inhibitory action of the amylase inhibitor is generally much faster than the decomposition rate of the substrate by the amylase (1), the amylase inhibitor may be added together with the macromolecular substance.

Subsequently, the conjugate is allowed to contact a water-insoluble macromolecular substance. The conjugate may usually be in the state of the reaction solution, and however, it may also be separated.

The macromolecular substance is able to be digested by the amylase (2), and it is usually a substrate of the amylase (2). The macromolecular substance is characterized by its insolubility in water. That is, contacting of the macromolecular substance with the amylase (2) portion of the conjugate occurs at the boundary between solid and solution, and as the result, steric hindrance of macromolecule(s) bound to the amylase (2) largely appears. This matter is supported by the experiment carried out by the inventor where a pentaose and an insoluble starch were digested by an α-amylase which was in its natural form or which was previously allowed to conjugate with a macromolecule. As the results of the experiment, the enzyme activity was scarcely lowered by the conjugate of the macromolecule in the case of the pentaose, while it was remarkably lowered in the case of the insoluble starch. The macromolecular substances include insoluble starches. When the macromolecular substance is water-soluble, it may also be used by the insolubilization of this substance. The insolubilization may be carried out by conjugation with an insoluble carrier material or by the polymerization of itself. For example, the water-soluble macromolecular substance is entrapped with agarose gel.

The conditions of the enzyme reaction may be determined according to the amylase (2) employed.

After the reaction, the amylase (2) activity is determined by detecting the changes of the reaction mixture, such as the increase of a decomposition product, the decrease of the raw material, etc.

According to the method of the invention, a biological ligand (1) in a sample containing an amylase derived from a high animal such as human serum can be detected and determined in high sensitivity and in high specificity. The method is simple, and a biological ligand (1) can easily and inexpensively be determined. The kind of the ligand (1) to be measured is not limited, and however, the present method is suitable for the ligand having a relatively high molecular weight. In the case of using the conjugate of the antibody and the amylase (2), since the ligand (1) is used only as the antigen which is necessary to produce the antibody, the amount of the ligand (1) can be very small. Accordingly, when only a small amount of the ligand (1) can be obtained or when the ligand (1) is extremely expensive, this method is effective.

Heretofore, the method of measuring a lower hapten such as digoxin and theophylline conjugated with an enzyme has been reported, but no method of measuring an extremely small amount such as ng/ml level of an antigen having a molecular weight of higher than 10,000 has been reported. The present invention offers a highly sensitive method of a macromolecular antigen, and it has raised the level of the determination from μg/ml to ng/ml.

EXAMPLE 1

(i) Preparation of CHM-induced α-amylase 1 mg of *Bacillus subtilis* α-amylase was dissolved in 1 ml of 0.1M phosphate buffer solution of pH 6.3 containing 10 mM o-phenanthroline. 100 μl of 2 mg/ml 4-maleimidomethyl cyclohexane-1-carboxylic acid N-hydroxy succinimide ester (CHMS) dimethylformamide (DMF) solution was added to this, and allowed to stand at room temperature for 1 hour. The reaction mixture was introduced into a SEPHADEX G-25 column, and gel filtration was carried out by using 0.1M phosphate buffer solution of pH 6.3. The void fractions were collected to obtain the desired CHM-induced amylase.

(ii) Preparation of HS-induced α-Fetoprotein 5 mg of α-fetoprotein was dissolved in 0.1M phosphate buffer solution of pH 6.0 containing 5 mM EDTA ethylenediamine tetracetic acid. 100 μl of 9 mg/ml S-acetylmercaptosuccinic anhydride (SAMS) DMF solution was added to this, and allowed to react at 37° C. for 1 hour. 110 μl of 1M hydroxylamine aqueous solution of pH 7.5 was added to the reaction mixture, and allowed to warm at 37° C. for 30 minutes. Subsequently, gel filtration using SEPHADEX G-25 was carried out as to the reaction mixture, and the void fractions were collected to obtain the desired HS-induced α-fetoprotein.

(iii) Preparation of conjugate of Amylase and α-fetoprotein

The above CHM-induced amylase solution was mixed with the HS-induced α-fetoprotein solution. The mixture was concentrated to 1 ml, and allowed to react at 4° C. overnight. The reaction solution was introduced into a SEPHACRYL S-300 column, and gel filtration was carried out by using 20 mM phosphate buffered saline solution of pH 7.0. The fractions containing the conjugate of which molar ratio was 1:3 were collected.

(iv) Measurement of α-Fetoprotein

Figure 1:
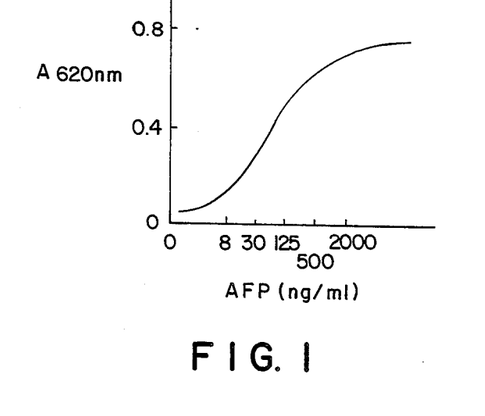
FIGS. 1, 6 and 7 shows the relationship between α-fetoprotein concentration and absorbance.

Each 50 μl of a human α-fetoprotein solution of which concentration was in the range of 0–2000 ng was mixed with 50 μl of a solution of the conjugate prepared in the above item (iii) to which 5% of polyethylene glycol 6,000 was added. 50 μl of a solution containing 100 μg/ml of α-amylase inhibitors mixture derived from wheat and 8 μg/ml anti-human-α-fetoprotein goat IgG was further added to each mixture, and allowed to react for 20 minutes. 1.0 ml of BLUE STARCH (made by Pharmacia Diagnostics A.B.) suspension was added to reaction mixture, and allowed to react at 37° C. for 20 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The relation between the α-fetoprotein concentration and the absorbance thus obtained is shown in FIG. 1.

Figure 2:
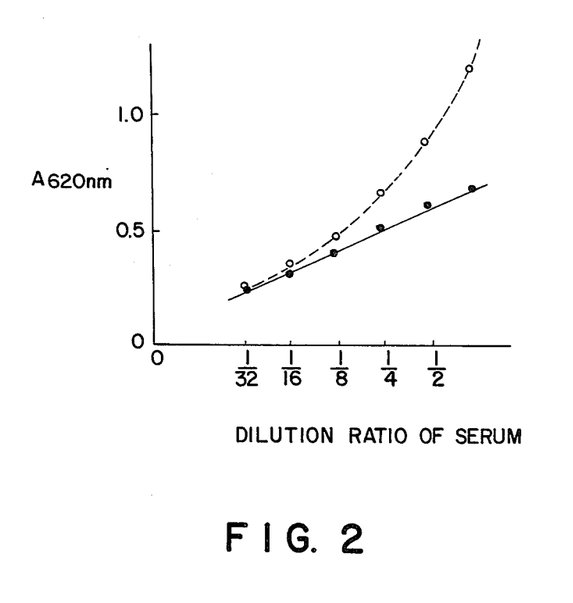
FIG. 2, depicts the relationship of the dilution ratio of serum and absorbance.

Subsequently, a human serum was diluted with a phosphate buffered saline solution (PBS) to prepare $2^n$ dilution series, and each 50 μl was placed in a small test tube. 50 μl of a solution of the conjugate prepared in item (iii) to which 10% of polyethylene glycol 6,000 was added and 50 μl of 8 μg/ml anti-human-α-fetoprotein goat IgG solution containing or not containing 100 μg/ml of amylase inhibitors mixture derived from wheat were added to each test tube, and allowed to react at 37° C. for 20 minutes. 1.0 ml of BLUE STARCH suspension was added to each reaction mixture, and allowed to react at 37° C. for 20 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The relation between the dilution ratio of the serum and the absorbance thus obtained is shown in FIG. 2. In the figure, closed circle indicates the case that the amylase inhibitor was added, and open circle indicates the case that it was not added. As can be seen from the figure, when the inhibitor was not added, the absorbance was raised by the amylase in the serum. Even at the dilution ratio of 32 times, the absorbance was slightly higher. On the other hand, when the inhibitor was added, the α-fetoprotein concentration was able to be determined without dilution nor a blank.

EXAMPLE 2

(i) Preparation of CHM-induced α-Amylase 5 mg of *Bacillus subtilis* α-amylase was dissolved in 1 ml of 0.1M phosphate buffer solution of pH 6.3 100 μl of 2 mg/ml CHMS DMF solution was added to this, and allowed to stand at room temperature for 1 hour. The reaction mixture was introduced into a SEPHADEX G-25 column, and gel filtration was carried out by using 0.1M phosphate buffer solution of pH 6.3. The void fractions were collected to obtain the desired CHM-induced amylase.

(ii) Preparation of Human IgG F(ab')$_2$ 10 mg of human IgG was dissolved in 2 ml of 0.1M acetate buffer solution of pH 4.0 containing 1 mM EDTA. 300 μg of pepsin was added to this, and stirred at 37° C. for 18 hours. The solution was adjusted to pH 6.0 by adding 0.1N NaOH, and introduced into a SEPHACRYL S-300 column which was previously equilibrated with 0.1M phosphate buffered 1 mM EDTA solution of pH 6.3, and eluted by the above phosphate buffer solution. A peak fractions corresponding to the molecular weight of about 100,000 were collected, and concentrated to 1 ml to obtain the desired human IgG F(ab')$_2$.

(iii) Preparation of the conjugate of Amylase and Human IgG Fab'

1 ml of 0.1M phosphate buffered 1 mM EDTA solution of pH 6.0 containing 6 mg of the above human IgG F(ab')$_2$ was mixed with 100 μl of 10 mg/ml 2-mercaptoethylamine hydrochloride aqueous solution, and stirred at 37° C. for 90 minutes. Gel filtration using a SEPHADEX G-25 column which was previously equilibrated with 0.1M phosphate buffer solution of pH 6.3 was carried out, and unchanged 2-mercaptoethylamine was removed to obtain HS-Fab'. 2 mg of CHM-induced α-amylase prepared in item (i) was added to the HS-Fab' solution thus obtained and allowed to react of 37° C. for 90 minutes. Subsequently, this reaction mixture was separated by gel filtration using a SEPHACRYL S-300 column which was equilibrated with 0.1M acetate buffered 5 mM calcium chloride solution of pH 6.0, and the fractions corresponding to the molecular weights of greater than 200,000 were collected. The fractions were concentrated to obtain the desired conjugate.

(iv) Measurement of Human IgG

Figure 3:
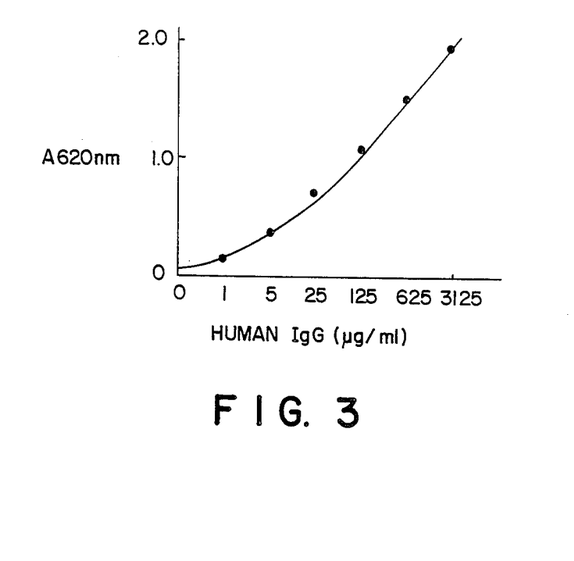
FIGS. 3 and 11 shows the relationship between human IgG concentration and absorbance.

Each 50 μl of a human IgG solution of which concentration was in the range of zero to 0.3125 μg/ml was mixed with 50 μl of a solution of the conjugate prepared in the above item (iii) to which 10% of polyethylene glycol 6,000 was added. 50 μl of a solution containing 100 μg/ml of the amylase inhibitor produced by Streptomyces viridosporus No. 297-A2 FERM-P 5405 and 100 μg/ml of anti-human IgG goat IgG was added to this, and allowed to react at 37° C. for 20 minutes. 1.0 ml of BLUE STARCH suspension was added to the reaction mixture, and further allowed to react at 37° C. for 10 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The relation between the human IgG concentration and the absorbance thus obtained is shown in FIG. 3.

EXAMPLE 3

(i) Preparation of CHM-induced α-Amylase 1 mg of Bacillus subtilis α-amylase was dissolved in 1 ml of 0.1M phosphate buffer solution of pH 6.3. 100 μl of 2 mg/ml CHMS DMF solution was added to this, and allowed to stand at room temperature for 1 hour. The reaction mixture was introduced into a SEPHADEX G-25 column, and gel filtration was carried out by using 0.1M phosphate buffer solution of pH 6.3. The void fractions were collected to obtain the object CHM-induced α-amylase.

(ii) Preparation of HS-induced IgE 5 mg of human IgE was dissolved in 0.1M phosphate buffer solution of pH 7.5 containing 5 mM EDTA. 100 μl of 9 mg/ml SAMS DMF solution was added to this, and allowed to react at 37° C. for 1 hour. 110 μl of 1M hydroxylamine aqueous solution of pH 7.5 was added to the reaction mixture, and allowed to warm at 37° C. for 30 minutes. Subsequently, gel filtration using SEPHADEX G-25 was carried out as to the reaction mixture, and the void fractions were collected to obtain the desired HS-induced IgE.

(iii) Preparation of conjugate of Amylase and of IgE

The above CHM-induced α-amylase solution was mixed with the HS-induced human IgE solution. The mixture was concentrated to 1 ml, and allowed to react at 4° C. overnight. The reaction solution was introduced into a SEPHACRYL S-300 column, and gel filtration was carried out by using 20 mM phosphate buffered saline solution pH 7.0. The fractions containing the conjugate of which molar ratio was 1:2 were collected.

(iv) Measurement of Human IgE

Figure 4:
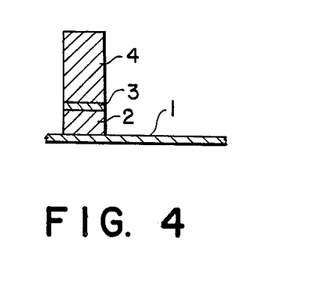
FIG. 4 shows a cross-section view of a coated polystyrene film used in the measurement of amylase activity using a reflectometer.
Figure 5:
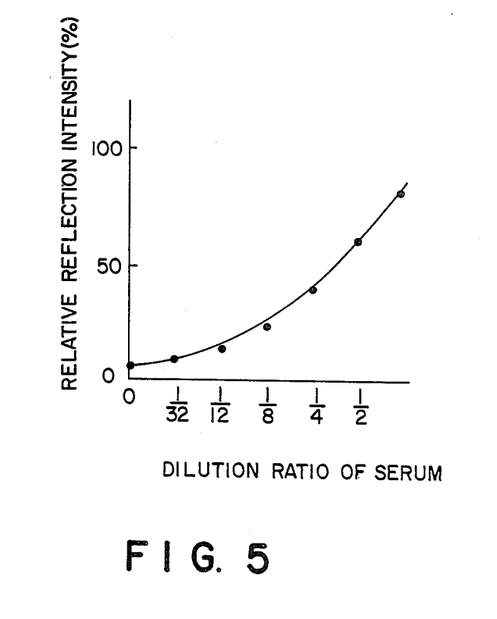
FIGS. 5 and 8 depicts the human IgE concentration and reflection intensity.

Each 50 μl of 10 μg/ml of a solution of the above conjugate was added to 50 μl of $2^n$ diluted human serum with PBS, and in order to inhibit human serum amylase, 50 μl of 500 μg/ml anti-human amylase goat IgG was added to the mixture. 50 μl of 10 μg/ml anti-human IgE goat IgG was further added, and allowed to react at 37° C. for 30 minutes. 100 μl of this reaction solution was dropped on a laminate film which consisting of polystyrene film 1, an anion-exchange resin layer 2, a reflection layer 3 and BLUE STARCH layer 4 as shown in FIG. 4. The amylase activity at room temperature after 20 minutes was measured by using a reflectometer. The relation between the human IgE concentration and the reflection intensity thus obtained is shown in FIG. 5.

EXAMPLE 4

(i) Preparation of CHM-induced α-Amylase 5 mg of Bacillus subtilis α-amylase was dissolved in 1 ml of 0.1M glycerophosphate buffer solution of pH 6.3 containing 10 mM o-phenanthroline. 100 μl of 2 mg/ml CHMS DMF solution was added to this, and allowed to stand at room temperature for 1 hour. The reaction mixture was introduced into a SEPHADEX G-25 column, and gel filtration was carried out by using 0.1M phosphate buffer solution of pH 6.3. The void fractions were collected to obtain the desired CHM-induced α-amylase.

(ii) Preparation of Anti-Human αFetoprotein Goat IgG F(ab')$_2$ 10 mg of anti-human α-fetroprotein goat IgG was dissolved in 2 ml of 0.1M acetate buffer solution of pH 4.0 300 μg of pepsin was added to this, and stirred at 37° C. for 18 hours. The solution was adjusted to pH 6.0 by adding 0.1N NaOH, and introduced into a SEPHACRYL S-300 column which was previously equilibrated with 0.1M phosphate buffered 1 mM EDTA solution of pH 6.3, and eluted by the above phosphate buffer solution. A peak fraction corresponding to the molecular weight of about 100,000 were collected, and concentrated to 1 ml to obtain the desired anti-human α-fetoprotein goat IgG F(ab')$_2$.

(iii) Preparation of conjugate of Amylase and Anti-Human α-Fetoprotein Goat IgG Fab'

1 ml of 0.1M phosphate buffered 1 mM EDTA solution of pH 6.0 containing 6 mg of the above anti-human α-fetoprotein goat IgG F(ab')$_2$ was mixed with 100 μl of 10 mg/ml 2-mercaptoethylamine hydrochloride aqueous solution, and stirred at 37° C. for 90 minutes. Gel filtration using a SEPHADEX G-25 column which was previously equilibrated with 0.1M phosphate buffer solution of pH 6.3 was carried out, and unchanged 2-mercaptoethylamine was removed to obtain HS-Fab'. 2 mg of CHM-α-amylase prepared in item (i) was added to the HS-Fab' solution thus obtained, and allowed to react at 37-C for 90 minutes. Subsequently, this reaction mixture was separated by gel filtration using a SEPHACRYL S-300 column which was equilibrated with 0.1M acetate buffered 5 mM calcium chloride solution of pH 6.0, and the fractions corresponding to the molecular weights of greater than 200,000 were collected. The fractions were concentrated to obtain the desired conjugate.

(iv) Measurement of α-Fetoprotein

Figure 6:
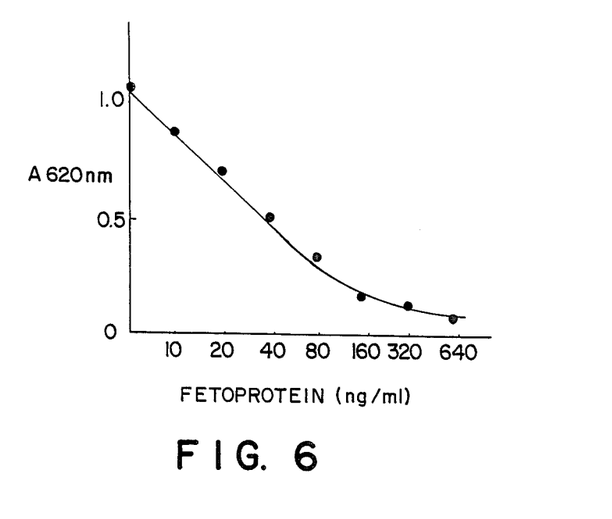

Each 100 μl of a human α-fetoprotein solution of which concentration was in the range of zero to 2000 ng was mixed with 50 μl of a solution of the conjugate prepared in the above item (iii) to which 100 μg/ml of the amylse inhibitor produced by *Streptomyces viridosporus* No. 297-A2 FERM-P 5405 and 7% of polyethylene glycol 6000 were added, and allowed to react at 37° C. for 30 minutes. 1.0 ml of BLUE STARCH suspension was added to the reaction mixture, and further allowed to react at 37° C. for 30 minutes. The enzyme reaction was terminated by adding 1 ml of 0.5N NaOH. The mixture was stirred, and then centrifuged at 3,500 rpm for 2 minutes. The absorbance of 620 nm of the supernatant was measured. The relation between the human α-fetoprotein concentration and the absorbance thus obtained is shown in FIG. 6.

Figure 7:
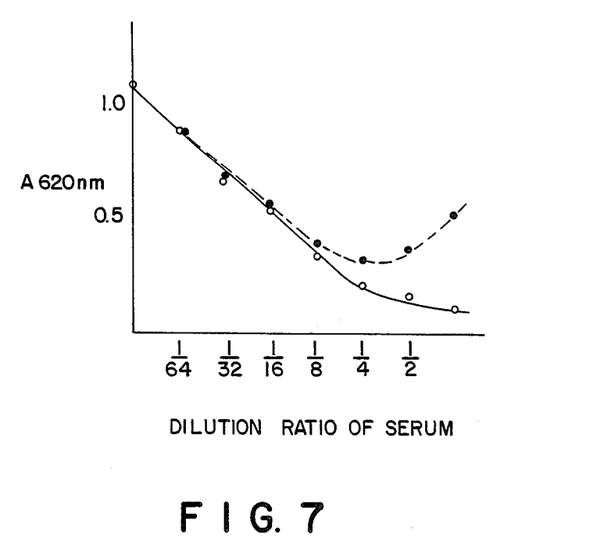

Subsequently, 100 μl of a human serum containing human α-fetoprotein was diluted with 20 mM glycerophosphate buffer solution of pH 6.0 to prepared $2^n$ dilution series. Each 100 μl was placed in a small test tube, and mixed with 100 μl of a solution of the conjugate prepared in item (iii) to which the amylate inhibitor produced by *Streptomyces viridosporus* No. 297-A2 FERM-P 5405 and 7% of polyethylene glycol 6,000 were added. The mixture was allowed to warm at 37° C. for 30 minutes. 1.0 ml of BLUE STARCH suspension was added to the reaction mixture, and further allowed to react at 37° C. for 30 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The results are shown in FIG. 7. In the figure, open circles indicate the case that the amylase inhibitor was added, and closed circles indicate the case that the amylase inhibitor was not added. As can be seen from the figure, when the amylase inhibitor was not added, the absorbance was raised by the amylase in the serum. While, when the amylase inhibitor was added, the α-fetoprotein was able to be determined without dilution nor a blank.

EXAMPLE 5

(i) Preparation of SPDP-α-Amylase 1 mg of Bacillus subtilis α-amylase was dissolved on 0.1M glycerophosphate buffer solution of pH 7.5 containing 10 mM o-phenanthroline. 100 μl of 1 mg/ml N-succinimidyl-3-(2-pyridyldithio) propionic acid (SPDP) DMF solution was added to this, and allowed to stand at room temperature for 30 minutes. The reaction mixture was introduced into a SEPHADEX G-25 column which was previously equilibrated with 0.1M glycerophosphate buffer solution of pH 7.5, and gel filtration was carried out to obtain 1 mg of SPDP amylase.

(ii) Preparation of Anti-Human IgE Goat igG F(ab')$_2$ 10 mg of anti-human IgE goat IgG was dissolved in 2 ml of 0.1M acetate buffer solution of pH 4.0. 300 μg of pepsin was added to this, and stirred at 37° C. for 18 hours. The solution was adjusted to pH 6.0 by adding 0.1N NaOH, and introduced into a SEPHACRYL S-300 column which was previously equilibrated with 0.1M phosphate buffered 1 mM EDTA solution of pH 6.3, and eluted by the above phosphate buffer solution. A peak fractions corresponding to the molecular weight of about 100,000 were collected, and concentrated to 1 ml to obtain the desired anti-human IgE goat IgG F(ab')$_2$.

(iii) Preparation of conjugate of Amylase and Anti-Human IgE Goat IgG Fab'

1 ml of 0.1M phosphate buffered 1 mM EDTA solution of pH 6.0 containing 6 mg of the above anti-human IgE goat IgG F(ab')$_2$ was mixed with 100 μl of 10 mg/ml 2-mercaptoethylamine hydrochloride aqueous solution, and stirred at 37° C. for 90 minutes. Gel filtration using a SEPHADEX G-25 column which was previously equilibrated with 0.1M glycerophosphate buffer solution of pH 7.5 was carried out, and unchanged 2-mercaptoethylamine was removed to obtain HS-Fab'. 2 mg of SPDP-α-amylase prepared in item (i) was added to the HS-Fab' solution thus obtained, and allowed to react at 4° C. for 18 hours. Subsequently, this reaction mixture was separated by gel filtration using a SEPHACRYL S-300 column which was equilibrated with 0.1M acetate buffered 5 mM calcium chloride solution of pH 6.5, and the fractions corresponding to the molecular weights of greater than 200,000 were collected. The fractions were concentrated to obtain the desired conjugate.

(iv) Measurement of Human IgE

Figure 8:
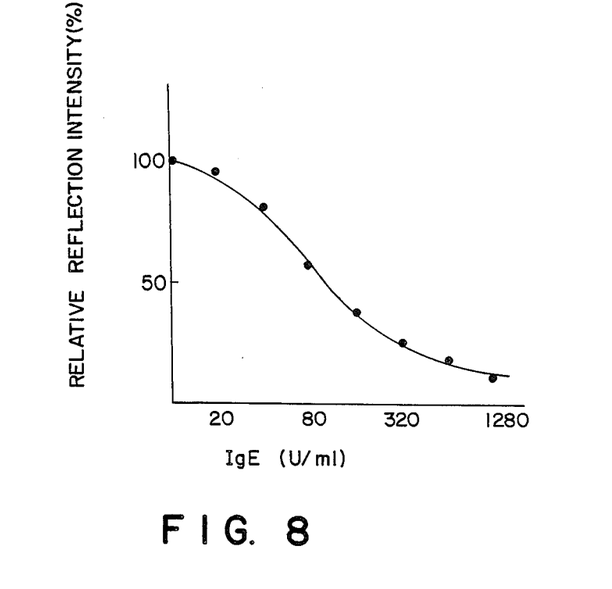

Each 50 μl of a human IgE solution of which concentration was in the range of 0.1280 U/ml was mixed with 50 μl of a solution of the conjugate prepared in the above item (iii) to which 100 μg/ml of the amylase inhibitors mixture derived from wheat and 7% of polyethylene glycol 6,000 were added, and allowed to react for 30 minutes. 50 μl of this reaction solution was dropped on a laminate film as shown in FIG. 4. The amylase activity at room temperature after 20 minutes was measured by using a reflectometer. The relation between the human IgE concentration and the reflection intensity thus obtained is shown in FIG. 8.

Subsequently, IgE concentration of 5 sera samples were measured by the method of the invention and the conventional sandwich EIA method. The results are shown below.

| Serum | IgE Concentration | |
|---|---|---|
| | The method of the invention | EIA method |
| 1 | 128 U/ml | 125 U/ml |
| 2 | 439 | 451 |
| 3 | 71 | 68 |
| 4 | 1190 | 1120 |
| 5 | 50 | 51 |

EXAMPLE 6

(i) Preparation of SPDP-α-Amylase 1 mg of SPDP-α-amylase was prepared from 1 mg of *Bacillus subtilis* amylase in the same manner as described in item (i) of Example 5.

(ii) Preparation of Anti-Human Albumin Goat IgG F(ab')$_2$ 10 mg of anti-human albumin goat IgG was dissolved in 2 ml of 0.1M acetate buffer solution of pH 4.0 300 μg of pepsin was added to this, and stirred at 37° C. for 18 hours. The solution was adjusted to pH 6.0 by adding 0.1N NaOH, and introduced into a SEPHACRYL S-300 column which was previously equilibrated with 0.1M phosphate buffered 1 mM EDTA solution of pH 6.3, and eluted by the above phosphate buffer solution. Peak fractions corresponding to the molecular weight of above 100,000 were collected, and concentrated to 1 ml to obtain the desired anti-human albumin goat IgG F(ab')$_2$.

(iii) Preparation conjugate of Amylase and Anti-Human Albumin Goat IgG Fab'

1 ml of 0.1M phosphate buffered 1 mM EDTA solution of pH 6.0 containing 6 mg of the above anti-human albumin goat IgG F(ab')$_2$ was mixed with 100 μl of 10 mg/ml 2-mercaptoethylamine hydrochloride aqueous solution, and stirred at 37° C. for 90 minutes. Gel filtration using a SEPHADEX G-25 column which was previously equilibrated with 0.1M glycerophosphate buffered solution of pH 7.5 was carried out, and unchanged 2-mercaptoethylamine was removed to obtain HS-Fab'. 1 mg of SPDP-α-amylase prepared in item (i) was added to the HS Fab' solution thus obtained, and allowed to react at 4° C. for 18 hours. Subsequently, this reaction mixture was separated by gel filtration using a SEPHACRYL S-300 column which was equilibrated with 0.1M acetate buffered 5 mM calcium chloride solution of pH 6.5, and the fractions corresponding to the molecular weight of greater than 200,000 were collected. The fractions were concentrated to obtain the desired conjugate.

(iv) Measurement of Human Albumin

Figure 9:
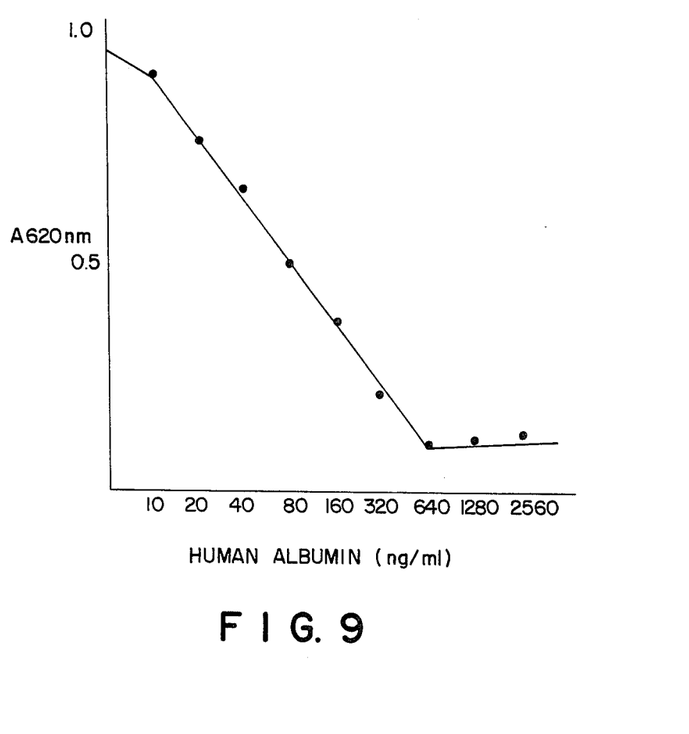
FIG. 9 shows relationship of human albumin and absorbance.

Each 100 μl of a human albumin solution of which concentrated was in the range of 0 to 2560 ng was placed in a small test tube, and mixed with 100 μl of the conjugate solution prepared in the above item (iii) to which 100 μg/ml of the amylase inhibitor produced by *Streptomyces viridosporus* No. 297-A2 FERM-P 5405 and 10% of polyethylene glycol 6,000 were added. Then, the mixture was allowed to reaction at 37° C. for 30 minutes. 1.0 ml of BLUE STARCH suspension was added to the reaction mixture, and further allowed to react at 37° C. for 30 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The results are shown in FIG. 9.

EXAMPLE 7

(i) Preparation of CHM-α-Amylase

CHM-α-amylase was prepared from *Bacillus subtilis* α-amylase in the same manner as described in item (i) of Example 4.

(ii) Preparation of Anti-Human Ferritin Mouse Monoclonal IgG F(ab')$_2$ 10 mg of anti-human ferritin mouse monoclonal IgG was dissolved in 2 ml of 0.1M acetate buffered 3 mM EDTA-0.1M cysteine solution of pH 5.5. 300 μg of pepsin was added to this, and stirred at 37° C. for 18 hours. The solution was adjusted to pH 6.0 by adding 0.1N NaOH, and introduced into a SEPHACRYL S-300 column which was previously equilibrated with 0.1M phosphate buffered 1 mM EDTA solution of pH 6.3, and eluted by the above phosphate buffer solution. Peak fractions corresponding to the molecular weight of about 100,000 were collected, and concentrated to 1 ml to obtain the object anti-human ferritin mouse monoclonal IgG F(ab')$_2$.

(iii) Preparation of the conjugate of Amylase and Anti-Human Ferritin Mouse Monoclonal IgG Fab'

1 ml of 0.1M phosphate buffered 1 mM EDTA solution of pH 6.0 containing 6 mg of the above anti-human ferritin mouse monoclonal IgG F(ab')$_2$ was mixed with 100 μl of 10 mg/ml 2-mercaptoethylamine hydrochloride aqueous solution, and stirred at 37° C. for 90 minutes. Gel filtration using a SEPHADEX G-25 column which was previously equilibrated with 0.1M phosphate buffer solution of pH 7.0 was carried out, and unchanged 2-mercaptoethylamine was removed to obtain HS-Fab'. 1 mg of CHM-α-amylase prepared in item (i) was added, and allowed to react at 37° C. for 90 minutes. Subsequently, this reaction mixture was separated by gel filtration using a SEPHACRYL S-300 column which was equilibrated with 0.1M acetate buffered 5 mM calcium chloride solution of pH 6.0, and the fractions corresponding to the molecular weights of greater than 200,000 were collected. The fractions were concentrated to obtain the desired conjugate.

(iv) Measurement of Ferritin in Human Serum

Figure 10:
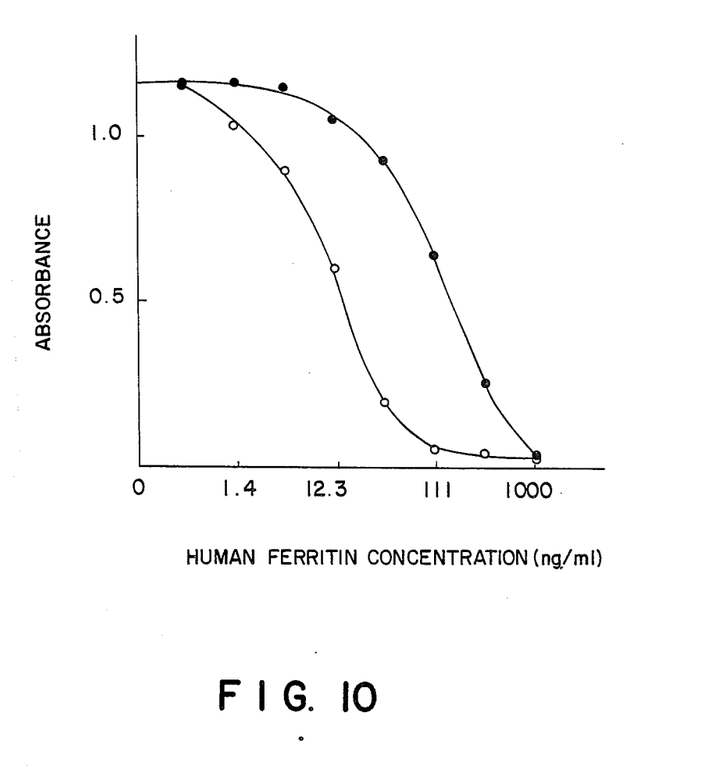
FIG. 10 depicts the relationship of ferritin in human serum and absorbance.

100 μl of a human serum containing human ferritin was diluted with goat serum to prepared $3^n$ dilution series. Each 100 μl was placed in a small test tube, and mixed with 100 μl of a solution of a conjugate prepared in the above item (iii) to which 100 μg/ml of the amylase inhibitor produced by *Streptomyces viridoporus* No. 297-A2 FERM-P 5405, 10 μg/ml of two kinds of anti-human ferritin monoclonal antibodies of which recognizing parts of ferritin are different determinants from the antibody of the conjugate and 7% of polyethylene glycol 6,000 were added. Then, the mixture was allowed to warm as 37° C. for 30 minutes. Subsequently, 1.0 ml of BLUE STARCH suspension was added to the reaction mixture, and further allowed to react at 37° C. for 30 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The results are shown in FIG. 10. In the figure, open circles indicate the case that the two kinds of the above anti-human ferritin monoclonal antibodies were added, and closed circles indicates the case that those were not added. As can be seen from the figure, the sensitivity was raised to about 10 times by adding the monoclonal antibodies.

EXAMPLE 8

(i) Preparation of CHM-α-Amylase

CHM-α-amylase was prepared from *Bacillus subtilis* α-amylase in the same manner as described in item (i) of Example 4.

(ii) Preparation of Anti-Human IgG Fc Specific Goat IgG F(ab')$_2$

Anti-human IgG goat F(ab')$_2$ (made by Cappel Laboratories Inc.) was passed through a SEPHAROSE 4B bound human IgG column which was buffered with 20 mM phosphate buffered 0.15M NaCl solution of pH 7.0. This column was washed with the above buffer solution, and eluted by 20 mM phosphate buffered 3M NaSCN solution of pH 7.0. Subsequently, the eluated was dialyzed against 0.1M phosphate buffered 1 mM EDTA solution of pH 6.0, and concentrated to obtain the desired anti-human IgG Fc specific goat IgG F(ab')$_2$.

(iii) Preparation of conjugate of α-Amylase and Anti-Human IgG Fc Specific Goat IgG Fab'

1 ml of 0.1M phosphate buffered 1 mM EDTA solution of pH 6.0 containing 6 mg of the above anti-human IgG Fc specific goat IgG F(ab')$_2$ was mixed with 100 μl of 10 mg/ml 2-mercaptoethylamine hydrochloride aqueous solution, and stirred at 37-C for 90 minutes. Gel filtration using a SEPHADEX G-25 column which was previously equilibrated with 0.1M phosphate buffer solution of pH 7.0 was carried out, and unreacted 2-mercaptoethylamine was removed to obtain HS-Fab'. 1 mg of CHM-induced α-amylase prepared in item (i) was added to the HS-Fab' solution thus obtained, and allowed to react at 37° C. for 90 minutes. Subsequently, this reaction mixture was separated by gel filtration using a SEPHACRYL S-300 column which was equilibrated with 0.1M acetate buffered 5 mM calcium chloride solution of pH 6.0, and the fractions corresponding to the molecular weights of greater than 200,000 were collected. The fractions were concentrated to obtain the desired conjugate.

(iv) Measurement of Human IgG

Figure 11:
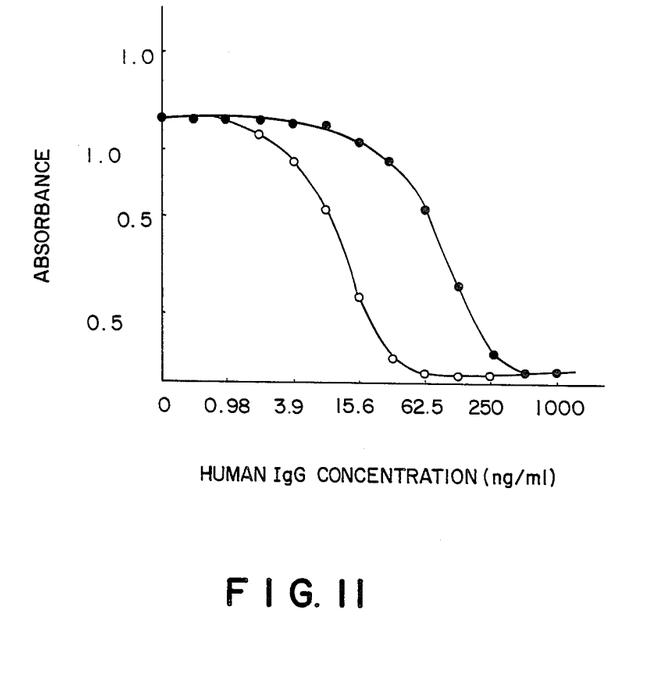

Each 100 μl of a human IgG solution of which concentration was in the range of zero to 1000 ng/ml was mixed with 100 μl of a solution of the conjugate prepared in the above item (iii) to which 7% of polyethylene glycol 6,000 was added, and allowed to react at 37° C. for 30 minutes. Subsequently, 50 μl of anti-human IgG Fab specific goat IgG (containing 10 μg) was added, and allowed to react at 37° C. for 30 minutes. 1.0 ml of BLUE STARCH suspension was added to the reaction mixture, and further allowed to react at 37° C. for 30 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The relation between the human IgG concentration and the absorbance thus obtained is shown in FIG. 11. In the figure, open circle indicates that the anti-human IgG Fab specific goat IgG was added, and closed circles indicate that it was not added. As can be seen from the figure, the sensitivity was raised to about 10 times by adding the anti-human IgG Fab specific goat IgG.

We claim:

1. A method of measuring a biological ligand (1) containing at least one antigenic determinant in a sample containing an amylase (1) derived from a higher animal which comprises:

using an antibody against said ligand (1), an amylase (2) not contained in said sample and bound to said antibody, an amylase inhibitor of which the inhibitory activity against said amylase (1) is stronger that that against said amylase (2) and a water-insoluble macromolecular substance capable of being digested by said amylase (2);

allowing said antibody to contact said ligand (1);

allowing said amylase inhibitor to contact said amylase (1) and said amylase (2);

allowing said amylase (2) to contact said macromolecular substance; and relating the amount of digestion of said macromolecular substance to the amount of said biological ligand (1) in said sample.

2. The method of claim 1, wherein a second antibody against a different antigenic determinant of said ligand (1) is further allowed to contact said ligand (1).

3. The method of claim 2, wherein said second antibody is bound to a macromolecular compound which is not a substrate of amylase and is water-soluble and of which the molecular weight is greater than 1,000 daltons.

4. The method of claim 1 or claim 2, wherein the antibodies are monoclonal antibodies.

5. The method of claim 1, wherein said sample is serum or urine and said amylase (1) is pancreatic amylase and/or salivary amylase.

6. The method of claim 1, wherein said ligand (1) is a member selected from the group consisting of hormones derived from endocrine glands, plasma proteins, viral antigens, bacteria, α-fetoprotein, and carcinoembryonic antigens.

7. The method of claim 1, wherein said antibody is a ligand binding fragment of immunoglobulin.

8. The method of claim 1, wherein said amylase (2) is α-amylase.

9. The method of claim 1, wherein said amylase inhibitor is a member selected from the group consisting of the amylase inhibitor derived from wheat, the amylase inhibitor produced by a microorganism of Streptomyces and an antibody against the amylase (1).

10. The method of claim 1, wherein said macromolecular substance is insoluble starch.

* * * * *